United States Patent [19]

Moszner et al.

[11] Patent Number: 5,733,968
[45] Date of Patent: Mar. 31, 1998

[54] MULTI-COMPONENT DENTAL CEMENT BASED ON CALCIUM HYDROXIDE

[75] Inventors: Norbert Moszner, Eschen; Ulrich Salz, Weissensberg; Volker Rheinberger, Vaduz, all of Germany

[73] Assignee: Ivoclar AG, Schaan, Germany

[21] Appl. No.: 746,157

[22] Filed: Nov. 6, 1996

Related U.S. Application Data

[63] Continuation of Ser. No. 336,679, Nov. 7, 1994, abandoned.

[30] Foreign Application Priority Data

Nov. 10, 1993 [DE] Germany .................. 43 39 009.9

[51] Int. Cl.[6] .................. C08J 3/00; C08K 3/08; C08L 23/00; C08F 4/44
[52] U.S. Cl. .................. 524/779; 523/115; 523/116; 523/118; 524/788; 526/191; 526/210; 526/212; 526/89; 526/219.6; 526/227; 526/316
[58] Field of Search .................. 523/115, 116, 523/118; 524/433, 436, 779, 788; 526/191, 316, 210, 212, 89, 219.6, 227

[56] References Cited

U.S. PATENT DOCUMENTS

| | | | |
|---|---|---|---|
| 3,607,834 | 9/1971 | Marx et al. | 526/316 |
| 5,241,006 | 8/1993 | Igbal et al. | 525/196 |
| 5,378,785 | 1/1995 | Mitra | 523/115 |

FOREIGN PATENT DOCUMENTS

| | | |
|---|---|---|
| 0 189 903 | 8/1986 | European Pat. Off. |
| 0 413 290 | 2/1991 | European Pat. Off. |
| 0 546 648 | 6/1993 | European Pat. Off. |
| 2 094 326 | 9/1992 | United Kingdom |

OTHER PUBLICATIONS

West et al., "The Infra-Red Spectra of Metal Acetylacetonates In The Sodium Chloride Region," J. Inorg Nucl. Che., 1958, vol. 5, pp. 295–303.

*Primary Examiner*—Patrick D. Niland
*Attorney, Agent, or Firm*—Nixon & Vanderhye P.C.

[57] ABSTRACT

The invention relates to a multi-component dental cement which contains as a first component an ethylenically unsaturated polymerisable compound, as a second component calcium hydroxide, calcium oxide or a precursor thereof and also a polymerisation initiator, the constituents of which can be contained in one or more cement components, which is characterized in that the ethylenically unsaturated polymerisable compound has both at least one β-dicarbonyl group and also at least one acrylic, alkacrylic or vinyl aromatic group. Also included are a process for the production of a multi-component dental cement and the use of the described polymerisable β-dicarbonyl compounds in calcium hydroxide dental cements.

17 Claims, No Drawings

MULTI-COMPONENT DENTAL CEMENT BASED ON CALCIUM HYDROXIDE

This is a continuation of application Ser. No. 08/336,679, filed Nov. 7, 1994, now abandoned.

The present invention relates to a multi-component dental cement based on calcium hydroxide which contains as a first component an ethylenically unsaturated polymerisable compound, as a second component calciumhydroxide, calcium oxide or a precursor thereof and also a polymerisation initiator. The cement hardens by chelation of the calcium ions and radical polymerisation of the ethylenically unsaturated monomers.

In dentistry, a series of so-called dental cements is used for example for the securing of crowns, inlays or orthodontic devices, as root-canal filling materials, as underfilling materials when introducing dental restoration materials or also as filling material itself. Dental cements consist for example of a mixture of fine-particled metal oxides or metal hydroxides which is brought to react with a mixing liquid which essentially contains phosphoric acids, polycarboxylic acids or also salicylic acid derivatives.

Such a metal hydroxide is for example calcium hydroxide. Calcium hydroxide has been used for more than 50 years inter alia because of its bactericidal effect and its stimulating effect on the secondary dentinification in dentistry (Hermann B. W.: Zahnärztliche Rundschau 1930, 39, p. 888). Mainly, it was or is used in the form of an aqueous suspension as underfilling material for the capping of pulp or as a temporary root inlay. The disadvan-tage of aqueous calcium hydroxide slurries is that this type of material shows no setting reaction and is also therefore scarcely loadable in mechanical terms. Calcium hydroxide slurries can therefore only be used in thin layers or temporarily. In contrast, calcium hydroxide cements which, as described in U.S. Pat. No. 3,047,408, contain salicylates show a setting reaction and therefore also a certain mechanical loadability. For this, an excess of calcium hydroxide is brought to react with a salicylic acid ester of a polyhydric alcohol, i.e. during the setting reaction the $Ca^{2+}$ ion is complexed by the salicylate, whereupon a polymeric network structure forms. In addition to the still relatively low mechanical loadability, these types of cement do however have other disadvantages. Firstly, the setting reaction proceeds very slowly and is very moisture-sensitive, i.e. this type of material shows no so-called command hardening, which is very important during the processing, e.g. the fitting of an underfilling, so that immediately after placing the underfilling, one can start to construct the actual filling. Secondly, this type of material suffers from a very intensive characteristic intrinsic odour.

Light-hardening cements have been brought onto the market in recent years to effect command hardening and to strengthen the mechanical loadability. In all cases these cements contain compounds having a methacrylate group which are polymerised by irradiation with a light catalyst which absorbs in the visible range.

Such systems are for example described in EP-A-0 189 903 and DE-A-38 01 207. According to EP-A-0 189 903, an underfilling material containing calciumhydroxide or an agent forming calcium hydroxide such as calcium oxide is described, which is photopolymerisable. This underfilling material contains ethylenically unsaturated compounds, including in particular vinyl urethane or urethane (meth) acrylate compounds, a photocatalyst, e.g. camphor quinone, in combination with an amine. The calcium hydroxide is not bound by means of chelation, but purely physically by inclusion in the polymer network. The corresponding product has come onto the market under the name "Prisma Dycal VLC". It is reported in the literature (Staehle, H. J., Calciumhydroxid in der Zahnheilkunde, Hanser, Munich 1990) that Prisma Dycal VLC shows only a minimum antimicrobial effect because of its slight solubility. In addition, only shallow hardening depths are achieved. According to DE-A-38 01 207, compounds are used in which a methacrylate function is combined with a salicylate function in one molecule. In addition to the disadvantage of the strong characteristic intrinsic odour which is also present in this system, there is the danger that the radical polymerisation is inhibited by the phenolic salicylate group. Reports are frequently found in literature (see e.g. Millstein, P. L., Nathanson, D., J. Prosthet. Dent. 1983, 50, 211) to the effect that the polymerisation of filling composites based on methacrylate is impaired by phenolic compounds (special eugenol).

In addition, known from EP-A-0 219 058 are polymerisable cement mixtures which contain a) polymerisable, unsaturated monomers and/or oligomers and/or polymers with acid groups and/or reactive acid derivative groups, b) fine-particled, reactive fillers which can react with these acids or acid derivatives, such as calcium hydroxide and c) hardening agents, whereby the acid groups or acid derivative groups present in the polymerisable compounds are able to lead ionically to a cement reaction with the fine-particled reactive fillers. These cement compositions do however have the disadvantage that in particular the described prepolymeric polyacids have to be additionally synthesized and purified in an expensive manner. Moreover, less filler is able to be incorpora-ted as the degree of polymerisation of the polyacids increases.

Brauer, G. M., White, E. E., Moshonas, M. G., J. Dent. Res. 1958, 37, 547 and Nielsen, T. L., Acta Odont, Scand. 1963, 21, 159 describe the use of acetyl acetone or acetoacetic acid ethyl ester in combination with ZnO as dental cement, but found that such combinations were unusable.

It is the object of the invention to provide a multi-component dental cement based on calcium hydroxide which does not have the aforementioned disadvantages and displays improved physical properties.

This object is achieved by a multi-component dental cement which contains as a first component an ethylenically unsaturated polymerisable compound, as a second component calcium hydroxide, calcium oxide or a precursor thereof and also a polymerisation initiator, the constituents of which can be contained in one or more cement components, and which is characterized in that the ethylenically unsaturated polymerisable compound has both at least one β-dicarbonyl group and at least one acrylic, alkacrylic or vinyl aromatic group.

The cement can in particular contain more than one of these ethylenically unsaturated polymerisable compounds.

The ethylenically unsaturated polymerisable compound can also have several β-dicarbonyl groups and/or several acrylic, alkacrylic or vinyl aromatic groups, e.g. 2 to 4 of each.

The alkacrylic group is preferably an acrylic group substituted with a $C_1$ to $C_{10}$ alkyl group, preferably $C_1$ to $C_5$ alkyl group and in particular a methacrylic group and the vinyl aromatic group is preferably a styrene or 4-vinyl benzyl group.

The ratio of the β-dicarbonyl groups to the ethylenically unsaturated polymerisable groups is preferably in the range from 5:1 to 1:5, in particular 3:1 to 1:3 and is most preferably 1:1.

According to a preferred embodiment, the ethylenically unsaturated polymerisable compound is a compound of the formula

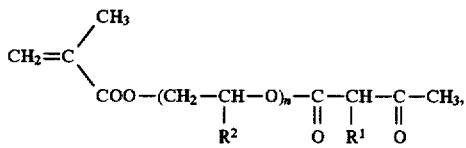 (I)

in which n=1 to 20, in particular 1 to 10, $R^1$=hydrogen or a $C_1$ to $C_{10}$ alkyl group, in particular hydrogen or a $C_1$ to $C_5$ alkyl group such as a methyl group and $R^2$=hydrogen or a $C_1$ to $C_{10}$ alkyl group, in particular hydrogen or a $C_1$ to $C_5$ alkyl group such as a methyl or ethyl group, or of the formula

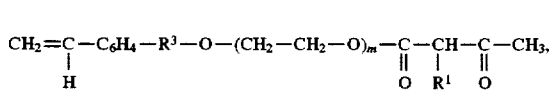 (II)

in which m=0 to 20, in particular 0 to 10, $R^1$=hydrogen or a $C_1$ to $C_{10}$ alkyl group, in particular hydrogen or a $C_1$ to $C_5$ alkyl group such as a methyl group and $R^3$=a $C_1$ to $C_{10}$ alkylene group, in particular a $C_1$ to $C_5$ alkylene group such as a methylene group.

These preferred compounds include in particular

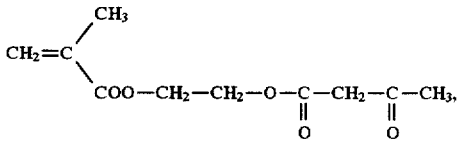 (I,1)

(Acetoacetoxyethyl methacrylate, AAEMA)

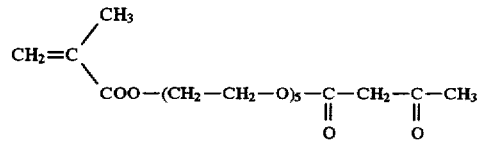 (I,2)

(Acetoaceto-PEG-200-methacrylate, PEG-200-AAMA)

or

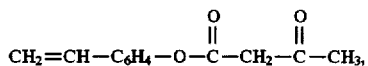 (II,1)

(Acetoacetic acid-4-vinyl benzyl ester, AASt).

The β-dicarbonyl compounds of formulae I and II according to the invention can for example be prepared according to the process described in DE-A-21 56 446 which is to be adapted to the specially used compounds if necessary. The compound (I, 1) is thus obtained in almost quantitative yield if one dissolves 1 mol of the corresponding hydroxy compound, 1 g triethylamine and 1 g 2,6-di-tert.-butyl-p-cresol in 500 ml absolute ethyl acetate, adds 88 g (1.05 mol) diketene dropwise to this solution within 1 hour with stirring, then heats the reaction mixture for ca. 2 hours under reflux, then after cooling, washes the product firstly with dilute HCl and then with water, and after drying with sodium sulphate, distils off the solvent (see e.g. also DE-A- 31 49 797). Moreover, compound (I,1) is available commercially from Lonza AG in 96% purity.

In analogous manner, the compounds (I, 2) and (II, 1) can be produced by reacting diketene with polyethylene glycol (PEG)-200-monomethacrylate and 4-vinyl benzyl alcohol in the presence of 1,4-diazabicyclo(2.2.2)-octane (DABCO). A corresponding process is also described in GB-A-1 144 486.

The multi-component dental cement according to the invention contains the ethylenically unsaturated polymerisable compound, preferably in a quantity from 7 to 70, in particular 7 to 60 and preferably 7 to 55 wt. %.

Moreover, additives customarily used in these type of cements can be present. These include monomers, initiators and accelerators and stabilisers and fillers.

Coming into question as examples of monomers are methyl methacrylate, triethylene glycol dimethacrylate, hexane diol dimethacrylate, dodecanediol dimethacrylate, Bisphenol-A-dimethacrylate, Bisphenol-A-glycidyl methacrylate, trimethylol propane trimethacrylate, hydroxethyl methacrylate and urethane dimethacrylate, e.g. the reaction products described in the following as urethane dimethacrylate from 1 mol hexamethylene diisocyanate or trimethyl hexamethylene diisocyanate with 2 mol 2-hydroxyethyl methacrylate or from 1 mol tri(6-isocyanatohexyl) biuret with 3 mol 2-hydroxyethylmethacrylate.

The known peroxides such as dibenzoyl peroxide, dilauryl peroxide, tert.-butyl peroctoate or tert.-butyl perbenzoate can be used as initiators for the hot polymerisation, although azobisisobutyroethyl ester, benzpinacol or 2,2-dimethyl benzpinacol are also suitable.

Benzophenone and benzoin and their derivatives for example can be used as initiators for the photopolymerisation. Moreover, α-diketones such as 9,10-phenanthrene quinone, diacetyl or 4,4'-dichlorobenzil can also be used. Camphor quinone (CC) is preferably used, the α-diketones in combination with amines such as cyanoethyl methylaniline, dimethyl aminoethyl methacrylate, triethanolamine or N,N-dimethyl-sym.-xylidine being particularly preferred as reducing agent.

Used as initiators for the cold polymerisation are radical-supplying systems, e.g. benzoyl-(BP) or lauryl peroxide together with amines such as N,N-dimethyl-sym.-xylidine, N,N-dimethyl-p-toluidine or 3,5-di-tert.-butyl-N,N'-diethylaniline (DABA).

Amorphous silicic acids are for example suitable as normal fillers, in particular pyrogenic and precipitated silicic acid with a BET surface of 30 to 300 m²/g (Aerosil 200, Ox 50) or zinc oxide (ZnO), whilst X-ray opaque glasses, barium sulphate or ytterbium fluoride are preferably used as X-ray opaque fillers and the inorganic components can be silanised in the usual way with e.g. 3-methacryloyloxypropyl trimethoxy silane (Ox 50 sil.).

Fine-particled chip or bead polymers can also be incorporated into the dental material. These homo- or copolymers of the usual mono- or polyfunctional methacrylates can in turn be filled with the described inorganic fillers, even the X-ray opaque ones.

To improve the storage stability, stabilisers are added to the materials, such as for example hydroquinone monomethyl ether (MEHQ) or 2,6-di-tert.-butyl-4-methylphenol (BHT).

Usual polymerisation initiators, which also include photoinitiators, are suitable as polymerisation initiators. Examples of suitable polymerisation initiators are benzoyl peroxide and camphor quinone.

During the reaction of the calcium hydroxide, the calcium oxide or the precursor material thereof with the ethylenically unsaturated, polymerisable β-dicarbonyl compound according to the invention, the corresponding calcium complexes are formed.

In order to be able to characterise these calcium complexes, they were prepared and isolated according to the following process. 20 mMol Ca compound were suspended (calcium hydroxide, calcium carbonate or calciumphosphate) or dissolved (calcium acetate or calcium chloride) in 70 ml water/ethanol (1:1). 10 ml of an ethanolic solution of 40 mMol AAEMA were added dropwise to this mixture with stirring at room temperature.

In the case of calcium chloride, carbonate, phosphate and acetate, a further 10 ml of a 2.0 molar ammonia solution were added dropwise. After a further 2 hours' stirring, the formed precipitate was filtered off, thoroughly washed with water and ethanol and dried in fine vacuum. The yield was 73.3% using calcium hydroxide, 31.4% using calcium chloride and 29.4% using calcium acetate. Analogous to this, the reaction of calcium hydroxide with acetic acid ester (EAA) as comparison example gave a yield of 68.8%. In addition, the reaction of calcium hydroxide with PEG-200-AAMA was carried out in analogous manner, whereby the formed complexes were very readily soluble both in water and in organic solvent and were therefore difficult to isolate.

Moreover, the Ca-AAEMA complex was obtainable according to the literature instructions by West, R., Riley, R., J. Inorg. Nucl. Chem. 1958, 5, 295, in 94.1% yield, whereby 0.10 mol metallic calcium were dissolved in 350 ml absolute ethanol by heating under reflux. After cooling to room temperature, 50 ml of a solution of 0.20 mol AAEMA in ethanol were added dropwise and the whole mixture stirred for 2 hours. The precipitate formed was filtered off and washed and then dried in fine vacuum. The Ca-AAEMA complex is soluble in DMF or dimethyl sulphoxide (DMSO).

The obtained Ca complexes were characterised by melting point, elemental analysis, residue on ignition, $^1$H-NMR- and IR spectroscopy.

Ca(AAEMA)$_2$

Fp.: 189°–191° C.

CaC$_{20}$H$_{26}$O$_{10}$(466.5): found: C: 50.26 (reported: 51.50), H: 5.66 (5.62);

residue on ignition: 12.74 (reported: 12.02 CaO);

$^1$H-NMR (DMSO-d$_6$): 1.72 (3H,s.CH$_3$—C(O$^-$)=), 1.90 (3H.s.CH$_3$—C=), 4.03–4.33 (4H,m,—CH$_2$—CH$_2$), 4.53 (1H, s,=CH—), 5.70 (1H,s) and 6.07 ppm (1H,s,CH$_2$=);

IR (KBr): 1719 (C=O), 1646 (C=O), 1530 cm$^{-1}$ (C=C).

Ca(EAA)$_2$: (Comparative example)

Residue on ignition: 18.80 (19.13 CaO);

$^1$H-NMR (DMSO-d$_6$): 1.22 (3H,t,—CH$_2$—CH$_3$), 1.71 (3H,s,CH$_3$—C(O$^-$)=), 3.92 (2H,q,CH$_2$—CH$_3$—), 4.49 ppm (1H,s,=CH—);

IR (KBr): 1642 (C=O), 1518 cm$^{-1}$ (C=C).

In the following example are described dental cement formulations according to the invention which contain AAEMA or PEG-200-AAMA as β-dicarbonyl compound according to the invention, the individual formulations differing from one another by virtue of different contents of these compounds.

The calcium hydroxide dental cement was prepared according to the following formulation.

| Base paste: | |
|---|---|
| Urethanediol dimethacrylate | 29.6 mass % |
| Butanediol dimethacrylate | 7.3 mass % |
| DABA | 0.3 mass % |
| MEHQ | 0.1 mass % |
| Ca(OH)$_2$ | 43.0 mass % |
| ZnO | 5.4 mass % |
| Ox 50 sil. | 14.3 mass % |
| Activator paste: | |
| AAEMA or AAEMA/urethane dimethacrylate mixture 53.90% AAEMA with 100% proportion; 26.95% AAEMA with 50% proportion; 8.10% AAEMA with 25% proportion; | 53.9 mass % |
| BaSO$_4$ | 39.9 mass % |
| Aerosil 200 | 3.9 mass % |
| Benzoyl peroxide 50-FT | 2.0 mass % |
| Camphor quinone | 0.3 mass % |

The AAEMA was used in pure form (100%) or mixed with urethane dimethacrylate (50%, 15%). In another case, PEG-200-AAMA was used in 50% mixture with urethane dimethacrylate.

The corresponding compositions were produced in the usual way by mixing in a kneader. The dental cements obtained were then characterised. For this, base and activator pastes were mixed in a volume ratio of 1:1. The values obtained are given in Table 1.

TABLE 1

Material properties of dental cement variants with AAEMA or PEG-200-AAMA as complexing agent or BASIC L (comparison) after water storage (WL) or lactic acid storage (ML)

| | | % AAEMA in the monomer mixture of the activator paste | | | | | Prisma VLC | |
|---|---|---|---|---|---|---|---|---|
| | | 100 | 50 | 50$^b$ | 15 | 50$^c$ | Basic L | Dycal ® |
| Bending strength (MPa): | 24 h WL | — | 40.40 | — | 74.80 | 34.70 | 13 | 29 |
| E-modulus (MPa): | 24 h WL | — | 2017 | — | 4411 | 1427 | — | 910 |
| Compressive strength (MPa): | without WL$^d$ | — | 152.10 | 173.30 | — | — | — | — |
| | 24 h WL | 59.30 | 148.70 | 142.40 | 197.10 | 115.60 | 75 | 180 |
| | 7 d WL | 24.00 | 131.10 | 55.60 | 199.40 | 49.90 | 76 | 190 |
| | 24 h ML | 51.00 | 173.30 | — | — | — | — | — |
| | 7 d ML | 22.80 | 190.50 | — | — | — | — | — |
| Water absorption (%) | | 29.7 | 12.8 | — | 1.8 | 13.1 | — | — |

TABLE 1-continued

Material properties of dental cement variants
with AAEMA or PEG-200-AAMA as complexing agent or BASIC L (comparison)
after water storage (WL) or lactic acid storage (ML)

| | | | | | | | |
|---|---|---|---|---|---|---|---|
| Water solubility (%) | 37.2 | 12.7 | — | 0.4 | 9.3 | 0.35 | — |
| Solubility in acid (mm) | 0.024 | 0.014 | — | insol. | insol. | 0.03 | — |

[b]Without exposure to light;
[c]use of PEF-200-AAMA instead of AAEMA;
[d]BASIC L (comparison) compressive strength: 75 MPa (24 h WL), 76 Mpa (7 d WL).
Composition of Basic L:

Base:

29.4 wt. % urethane dimethacrylate
7.3 wt. % butanediol dimethacrylate
43.3 wt. % Ca(OH)$_2$
14.2 wt. % Ox 50
5.4 wt. % ZnO
0.3 wt. % DABA
0.1 wt. % MEHQ
(The base/catalyst mixing ratio = 1:1)
Composition of Prisma VCL Dycal ®:

Catalyst:

24.0 wt. % 1,3-butanediol salicylate
24.0 wt. % trimethyl hexanediol disalicylate
6.0 wt. % methyl salicylate
40.0 wt. % barium sulphate
3.9 wt. % Aerosil 200
2.0 wt. % BP
0.1 wt. % CC 61.6 wt. % monomer
18.9 wt. % barium sulphate
18.9 wt. % Ca(OH)$_2$ The results prove the improved physical properties of the calcium hydroxide cements produced according to the invention, in particular the improved bending strength and the improved E-modulus and, viewed overall, that the mechanical strength of these cements is utilisable.

The processing range of the dental cements according to the invention is between 40 and 80 seconds and the thorough hardening depth is 6mm (40 sec. irradiation time; Heliomat (Vivadent); 80% AAEMA).

Compared with this are:

Basic L 2.0 mm (40 sec. irradiation time)

Prisma VCL Dycal® 1.4 mm (40 sec. irradiation time)

Adherence to the dentine is not observed. This can be explained by the fact that the β-dicarbonyl compounds react with the Ca(OH)$_2$ present (excess), i.e. complete complexation takes place.

We claim:

1. A multi-component dental cement comprising as a first component a monomeric ethylenically unsaturated polymerisable compound and a second component selected from the group consisting of calcium hydroxide and calcium oxide and a polymerisation initiator, the constituents of which can be contained in one or more cement components, wherein the monomeric ethylenically unsaturated polymerisable compound has both one to four β-dicarbonyl groups and one to four acrylic, alkacrylic or vinyl aromatic groups, said monomeric compound having a molecular weight of 218 to 923.

2. Multi-component dental cement according to claim 1, wherein the alkacrylic group is a methacrylic group and the vinyl aromatic group is a styrene group.

3. Multi-component dental cement according to claim 1, wherein the ratio of the β-dicarbonyl groups to the ethylenically unsaturated polymerisable groups is in the range of 3:1 to 1:3.

4. Multi-component dental cement according to claim 1 wherein the ethylenically unsaturated polymerisable compound is a compound of the formula

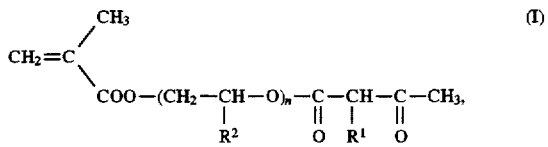

in which n=1 to 10, $R^1$=hydrogen or a $C_1$ to $C_{10}$ alkyl group, and $R^2$=hydrogen or a $C_1$ to $C_{10}$ alkyl group, or of the formula

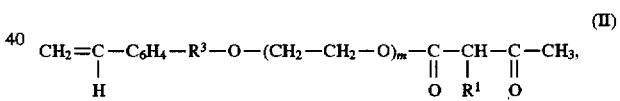

in which m=0 to 10, $R^1$=hydrogen or a $C_1$ to $C_{10}$ alkyl group, and $R^3$=a $C_1$ to $C_{10}$ alkylene group.

5. Multi-component dental cement according to claim 4, wherein the ethylenically unsaturated polymerisable compound is

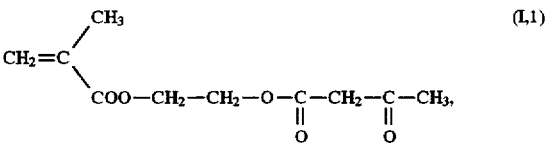

(Acetoacetoxyethyl methacrylate, AAEMA)

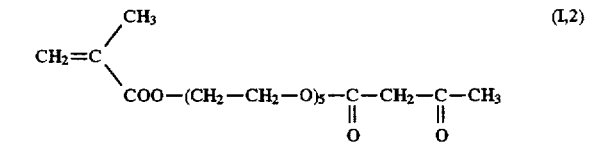

(Acetoaceto-PEG-200-methacrylate, PEG-200-AAMA)

or

-continued

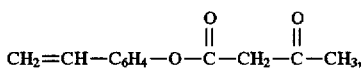
(II,1)

(Acetoacetic acid-4-vinyl benzyl ester, AASt).

6. Multi-component dental cement according to claim 1, further comprising a customary additive selected from the group consisting of an initiator, accelerator, stabiliser and filler.

7. Multi-component dental cement according to claim 1, wherein the ethylenically unsaturated polymerisable compound is present in a quantity of from 7 to 70 wt. %.

8. Multi-component dental cement according to claim 1, wherein the ethylenically unsaturated polymerisable compound has multiple β-dicarbonyl groups or acrylic, alkacrylic or vinyl aromatic groups.

9. Process for the production of a multi-component dental cement according to claim 1, comprising producing a) a base paste comprising said second component and b) an activator paste comprising the first component and mixing paste (a) and paste (b) together.

10. Multi-component dental cement according to claim 3 wherein the ratio is 1:1.

11. Multi-component dental cement according to claim 4 wherein
   $R^1$ and $R^2$ of formula (I) are hydrogen or a $C_1$ to $C_5$ alkyl group,
   $R^1$ of formula (II) is hydrogen or a $C_1$ to $C_5$ alkyl group and
   $R^3$ of formula (II) is a $C_1$ to $C_5$ alkylene group.

12. Multi-component dental cement of claim 7 wherein the ethylenically unsaturated polymerizable compound is present in a quantity of from 7 to 60 wt. %.

13. Multi-component dental cement of claim 12 wherein the ethylenically unsaturated polymerizable compound is present in a quantity of from 7 to 55 wt. %.

14. Multi-component dental cement comprising as a first component monomeric ethylencially unsaturated polymerisable compound, as a second component calcium hydroxide, calcium oxide, or a precursor thereof selected from the group consisting of calcium carbonate, calcium phosphate, calcium chloride and calcium acetate, and a polymerization initiator, the constituents of which can be contained in one or more cement components, wherein the monomeric ethylencially unsaturated polymerisable compound has both 1 to 4 β-dicarbonyl groups and 1 to 4 acrylic, alkacrylic or vinyl aromatic groups, said monomeric compound having a molecular weight of 218 to 923.

15. Process for the production of the multi-component dental cement according to claim 1, comprising producing (a) a base paste comprising the calcium hydroxide, calcium oxide or a precursor thereof selected from the group consisting of calcium carbonate, calcium phosphate, calcium chloride and calcium acetate, and (b) an activator paste comprising the ethylenically unsaturated polymerisable compound, and mixing paste (a) and paste (b) together.

16. Multi-component dental cement comprising as a first component monomeric ethylenically unsaturated polymerisable compound, as a second component calcium hydroxide, calcium oxide or a precursor thereof selected from the group consisting of calcium carbonate, calcium phosphate, calcium chloride and calcium acetate, and a polymerisation initiator, the constituents of which can be contained in one or more cement components, wherein the monomeric ethylencially unsaturated polymerisable compound has both a β-dicarbonyl group and an acrylic, alkacrylic or vinyl aromatic group, said monomeric compound having a molecular weight of 218 to 923.

17. A method of securing a crown, inlay or orthodontic device to a tooth comprising contacting said crown, inlay or orthodontic device and said tooth with the dental cement according to claim 1 and effecting hardening of said cement.

* * * * *

UNITED STATES PATENT AND TRADEMARK OFFICE

CERTIFICATE OF CORRECTION

PATENT NO. : 5,733,968
DATED : March 31, 1998
INVENTOR(S) : MOSZNER et al

It is certified that error appears in the above-identified patent and that said letters patent is hereby corrected as shown below:

On the title page,

Delete "[75] Inventors: Norbert Moszner, Eschen; Ulrich Salz, Weissensberg; Volker Rheinberger, Vaduz, all of Germany" and insert --[75] Inventors: Norbert Moszner, Eschen, Liechtenstein; Ulrich Salz, Weißensberg, Germany; Volker Rheinberger, Vaduz, Liechtenstein--; and Delete "[73] Assignee: Ivoclar AG, Schaan, Germany" and insert --[73] Assignee: Ivoclar AG, Schaan, Liechtenstein--.

Signed and Sealed this

Fourth Day of May, 1999

Attest:

Attesting Officer

Q. TODD DICKINSON

Acting Commissioner of Patents and Trademarks